(12) United States Patent
Farida et al.

(10) Patent No.: US 10,421,713 B2
(45) Date of Patent: Sep. 24, 2019

(54) PROCESS FOR PREPARING 4[[(BENZOYL)AMINO]SULPHONYL]BENZOYL CHLORIDES AND PREPARATION OF ACYLSULPHAMOYLBENZAMIDES

(71) Applicant: BAYER CROPSCIENCE AKTIENGESELLSCHAFT, Monheim am Rhein (DE)

(72) Inventors: Taraneh Farida, Pulheim-Geyen (DE); Hubertus Stakemeier, Bergisch Gladbach (DE); Jan Vermehren, Idstein (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/644,493

(22) Filed: Jul. 7, 2017

(65) Prior Publication Data

US 2017/0305845 A1  Oct. 26, 2017

Related U.S. Application Data

(62) Division of application No. 15/024,352, filed as application No. PCT/EP2014/071388 on Oct. 7, 2014, now Pat. No. 9,725,409.

(30) Foreign Application Priority Data

Oct. 10, 2013 (EP) .................... 13188179

(51) Int. Cl.
| | |
|---|---|
| *C07C 303/40* | (2006.01) |
| *C07C 311/16* | (2006.01) |
| *C07C 311/51* | (2006.01) |
| *C07D 303/40* | (2006.01) |
| *C07C 303/36* | (2006.01) |

(52) U.S. Cl.
CPC .......... *C07C 303/40* (2013.01); *C07C 311/16* (2013.01); *C07C 311/51* (2013.01); *C07D 303/40* (2013.01); *C07C 303/36* (2013.01)

(58) Field of Classification Search
None
See application file for complete search history.

(56) References Cited

U.S. PATENT DOCUMENTS

| | | | |
|---|---|---|---|
| 6,251,827 B1 | 6/2001 | Ziemer et al. | |
| 2005/0004372 A1 | 1/2005 | Pazenok et al. | |
| 2018/0118670 A1* | 5/2018 | Farida ................... | C07C 303/40 |

FOREIGN PATENT DOCUMENTS

| | | |
|---|---|---|
| WO | 9916744 A1 | 4/1999 |
| WO | 2005000797 A1 | 1/2005 |

OTHER PUBLICATIONS

Schotten-Baumann ("Schotten-Baumann Reaction (Schotten-Baumann Acylation)" Comprehensive Organic Name Reactions and Reagents, 2010, 573, p. 2536-2539).*
White ("Development of a Continuous Schotten-Baumann Route to an Acyl Sulfonamide" Org. Process Res. Dev., Published Apr. 12, 2012, vol. 16, p. 939-957).*
International Search Report of PCT/EP2014/071388 dated Oct. 30, 2014.

* cited by examiner

*Primary Examiner* — Amy C Bonaparte
(74) *Attorney, Agent, or Firm* — McBee Moore Woodward & Vanik IP, LLC

(57) ABSTRACT

Process for preparing compound of formula (Ia)

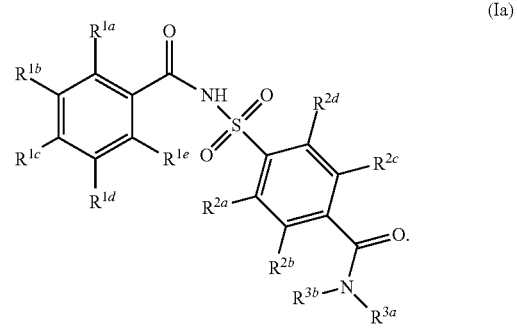

14 Claims, No Drawings

PROCESS FOR PREPARING 4[[(BENZOYL)AMINO]SULPHONYL]BENZOYL CHLORIDES AND PREPARATION OF ACYLSULPHAMOYLBENZAMIDES

CROSS REFERENCE TO RELATED APPLICATIONS

This application is a division of U.S. application Ser. No. 15/024,352, filed Mar. 23, 2016, which is a § 371 National Stage Application of PCT/EP2011/071388, filed Oct. 7, 2014, which claims priority to European 13188179.9 filed Oct. 10, 2013, the contents of each are incorporated herein in their entireties.

BACKGROUND

Field of the Invention

The invention relates to an improved process for preparing 4-[[(benzoyl)amino]-sulphonyl]benzoyl chlorides.

More particularly, the invention relates to an improved process for preparing 4-[[(2-methoxybenzoyl)amino]sulphonyl]benzoyl chloride and to the use thereof for preparing N-[4-(cyclopropylcarbamoyl)phenylsulphonyl]-2-methoxybenzamide.

N-[4-(Cyclopropylcarbamoyl)phenylsulphonyl]-2-methoxybenzamide (N-[4-(cyclo-propylcarbamoyl)phenyl-sulphonyl]-o-anisamide) is also referred to as cyprosulfamide. Cyprosulfamide is used as a safener in conjunction with a herbicide, or with a plurality of different herbicides. A safener serves to improve the selectivity of the herbicides used with respect to the crop plants of the particular crop being treated. The term "selectivity" refers to the crop plant compatibility of a herbicide.

Description of Related Art

Document WO 99/16744 discloses acylsulphamoylbenzamide derivatives and the preparation and use thereof as safeners. However, the preparation processes disclosed in WO 99/16744 relate to the laboratory scale and are found to be not particularly suitable for the industrial preparation of the compounds.

A two-stage process which has likewise been developed for use on the industrial scale for preparation of acylsulphamoylbenzamides is known from document WO 2005/000797 A1. Solvents proposed for the performance of the process known from WO 2005/000797 A1, as well as nonpolar silicone oils, are nonpolar and polar organic solvents.

Organic solvents mentioned explicitly are aliphatic and aromatic hydrocarbons, namely alkanes, for example heptane, octane or alkylated benzenes, for example toluene, dimethylbenzene (xylene), trimethylbenzene or paraffin oil. WO2005/000797 A1 also discloses halogenated aliphatic hydrocarbons, for example dichloromethane or halogenated aromatic hydrocarbons, for example chlorobenzene, dichlorobenzene or haloalkylbenzenes, for example benzotrifluoride.

In contrast, carboxylic esters are not mentioned in WO 2005/000797 A1 as suitable solvents and are accordingly not envisaged for performance of the two-stage process. Nor are ketones, acetamides, nitriles or ethers envisaged as solvents for performance of the two-stage process known from WO 2005/000797 A1. On the basis of the synthesis examples disclosed in WO 2005/000797 A1, in which only the two nonpolar organic solvents chlorobenzene and toluene are used, chlorobenzene and toluene should be considered to be preferred solvents according to the teaching of WO 2005/000797 A1.

There are various reasons for the problem of reduced yields, or the problem of varying yields, in the preparation of 4-[[(2-methoxybenzoyl)amino]sulphonyl]benzoyl chloride. Two of the probably particularly significant reasons are elucidated hereinafter.

The first reason relates to the formation of unwanted dimers. Only after intensive analysis of the first synthesis step, which serves for provision of the 4-[[(2-methoxybenzoyl)-amino]sulphonyl]benzoyl chloride precursor required for formation of cyprosulfamide, was it found that the reactants used for synthesis of said precursor, i.e. the ortho-methoxybenzoic acid compounds of the formula (III) and the 4-sulphamoylbenzoic acid compounds of the formula (IV), are not converted fully because of the formation of dimers when the chlorobenzene solvent is used.

The second reason relates to the further problems connected to the dimer formation in the case of use of the 4-[[(2-methoxybenzoyl)amino]sulphonyl]benzoyl chloride prepared in the process known from WO 2005/000797 A1 in the subsequent process step for preparation of the cyprosulfamide safener. Thus, the incomplete conversion of the abovementioned reactants used for synthesis of the precursor in the process step which serves for preparation of cyprosulfamide promotes the formation of unwanted by-products consisting of the active cyprosulfamide ingredient.

A further unwanted by-product probably forms through condensation of cyprosulfamide with 4-sulphamoylbenzoic acid compounds of the formula (IV).

For the synthesis of 4-[[(2-methoxybenzoyl)amino]sulphonyl]benzoyl chloride in chlorobenzene, WO 2005/000797 A1 (example 1) discloses a yield of 93%. No figures are given as to the extent of dimer formation in connection with example 1, although page 6 lines 21 to 22 of the description of WO 2005/000797 A1 makes it clear in general terms that the formation of unwanted dimers is also to be avoided by the process disclosed in WO 2005/000797 A1.

Nevertheless, it has been found in practice that the problem of dimer formation is not in fact avoided to an optimal degree by the processes known from the prior art. For example, even the filtration of the reaction product of the formula (II) was found to be problematic when the known process was employed on the industrial scale. Moreover, the improved process was to feature increased robustness compared to the known processes. The robustness of a process employable on the industrial scale relates, for example, to the filterability of the reaction solution in the case of varying amounts of product, and the requirement that, on completion of the reaction, the yields does not decrease significantly even if stirring of the reaction mixture continues for a prolonged period.

The requirement for continued stirring of a reaction mixture is not essential for the industrial scale implementation of a reaction. For instance, it may be unavoidable in practice for technical reasons alone that a reaction mixture, on completion of the reaction, is stirred for several more hours, for example overnight. In such a case, the robustness of a process is important.

SUMMARY

Against this background, the problem addressed by the invention was that of providing an improved process for preparing 4-[[(benzoyl)amino]sulphonyl]benzoyl chlorides (amide chloride compounds) of the formula (II) proceeding from ortho-methoxybenzoic acid of the formula (III) and 4-sulphamoylbenzoic acid of the formula (IV), where the improved process is to feature high robustness combined with simultaneously high yields.

The problem is solved by a process for preparing 4-[[(benzoyl)amino]sulphonyl]benzoyl chlorides of the formula (II)

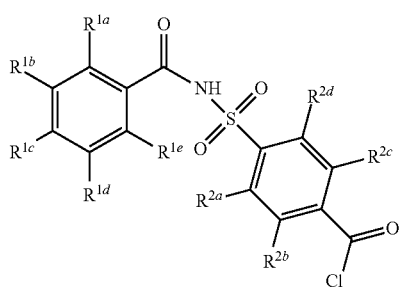

(II)

In which the $R^{1a}$ to $R^{1e}$ radicals and the $R^{2a}$ to $R^{2d}$ radicals are each independently selected from the group consisting of hydrogen, halogen, (C1-C6)-alkyl, (C1-C6)-haloalkyl, (C1-C6)-alkoxy, (C3-C7)-cycloalkyl, (C1-C6)-alkylthio, (C3-C7)-cycloalkylthio, S(O)q-(C1-C6)-alkyl with q=0, 1 or 2, (C1-C6)-alkylcarbonyl, —CO-aryl, cyano and nitro or in which any two adjacent R1a to R1e radicals form an —O—CH2CH2-radical,
proceeding from a compound of the formula (III)

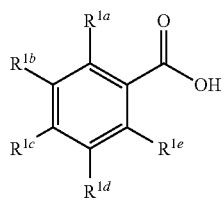

(III)

in which the $R^{1a}$ to $R^{1e}$ radicals are each as defined above, and a compound of the formula (IV)

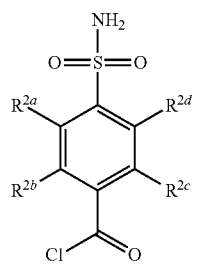

(IV)

in which the $R^{2a}$ to $R^{2d}$ radicals are each as defined above, by reacting compounds of the formula (III) and (IV) as reactants
  in a solvent selected from the group of the aprotic polar solvents, or
  in a solvent composition comprising at least one solvent selected from the group of the aprotic polar solvents.

DETAILED DESCRIPTION OF A PREFERRED EMBODIMENT

The invention relates to the optimization of the yield and to the improvement of the robustness of the process. Because of the comparatively large amounts of product in industrial manufacture, even only a slight improvement in the yield is of great significance from an economic point of view. An improvement in the purity of the product may also be of great significance in economic terms. Therefore, the improvement of a process performable on the industrial scale through variation of all the reaction parameters in industrial active ingredient preparation is fundamentally a constant endeavour. However, the variation of the parameters, in spite of the systematic procedure, is often not a matter of routine testing. In fact, the process optimization is by no means rarely a procedure of trial and error.

Specifically the unexpectedly strong influence of a particular solvent group on a chemical reaction can only be recognized and explained retrospectively.

Thus, in the variation of the reaction parameters in connection with the present invention, it was only clear retrospectively that the selection of solvent is of surprisingly great significance. The relevance of the solvent became particularly clear through the comparison of the yields of reactions that were conducted using various solvents, with prolonged continued stirring of the respective reaction solutions.

It was also found that, when the two solvents toluene and chlorobenzene used with particular suitability in the prior art for preparation of 4-[[(2-methoxybenzoyl)amino]-sulphonyl]benzoyl chloride are used, higher dimer formation is found than when one of the aprotic polar solvents used in accordance with the invention is used. The advantages of the use of aprotic polar solvents are apparent in the overview from Table 1.

What is particularly surprising is that, through the exchange of the solvents for an aprotic polar solvent, various problems associated with dimer formation can simultaneously also be avoided.

The subsequent problems include filtration problems at amide chloride stage, i.e. the filtration of the reaction solution that arises in the preparation of 4-[[(2-methoxy-benzoyl)amino]sulphonyl]benzoyl chloride is found to be difficult in practice.

A further problem is the reduction in the yield both for the stage of amide chloride preparation and for the stage of cyprosulfamide preparation, and the simultaneous deterioration in the quality, i.e. the purity, of the two products.

These problems can be avoided through the use of aprotic polar solvents.

Aprotic polar (dipolar) solvents are chemical compounds which have the feature that they do not eliminate any protons and are simultaneously polar.

In a formal sense, carboxylic esters are also assigned in the literature, in spite of their polarity, to the group of the aprotic nonpolar solvents. In connection with the present invention, therefore, for reasons of clarity, it is stated that, in the case of the present invention, carboxylic esters, especially the esters of propionic acid and of acetic acid, for example isopropyl acetate, are counted as part of the group of the aprotic polar solvents. The chlorobenzene solvent, in contrast, in spite of its high dipole moment, is hydrophobic in water and hence barely soluble, i.e. chlorobenzene is nonpolar. Toluene also forms part of the group of the nonpolar solvents.

The core of the invention relates to the finding that specifically aprotic and simultaneously polar solvents suppress the formation of dimers in amide chloride preparation, such that it is possible through the improved reaction regime to obtain compounds of the formula (II) with higher yields.

The aprotic polar compounds suitable as solvents in accordance with the invention must be chemically stable and distillable, and should also have a molecular mass (molecular weight) below 200. Because of the upper molecular weight limit, these solvents are characterized by a comparatively low boiling point. Thus, the selection of the useful solvents simultaneously fixes an upper limit for the reaction temperature. This upper temperature limit simultaneously results in a safeguarding function and constitutes an additional advantage in the implementation of the preparation process on the technical scale and on the industrial scale with respect to the reaction regime.

The process according to the invention is preferably employable for preparation of compounds of the formula (II) in which the $R^{1a}$ to $R^{1e}$ and $R^{2a}$ to $R^{2d}$ radicals are each independently selected from the group consisting of
hydrogen, fluorine, chlorine, bromine,
($C_1$-$C_6$)-alkyl, where the alkyl radical is branched or unbranched and is unsubstituted or substituted by one or more substituents selected from the group consisting of ($C_1$-$C_4$)-alkoxy and ($C_3$-$C_7$)-cycloalkyl,
($C_1$-$C_6$)-haloalkyl, where the alkyl radical is unsubstituted or substituted by one or more substituents selected from the group consisting of fluorine, chlorine, bromine and iodine,
($C_3$-$C_7$)-cycloalkyl, where the cycloalkyl radical is unsubstituted or substituted by one or more substituents selected from the group consisting of ($C_1$-$C_4$)-alkyl or ($C_3$-$C_7$)-cycloalkyl or ($C_1$-$C_4$)-alkoxy,
($C_1$-$C_6$)-alkoxy, where the alkoxy radical is branched or unbranched and is unsubstituted or substituted by one or more substituents selected from the group consisting of ($C_1$-$C_4$)-alkoxy and ($C_3$-$C_7$)-cycloalkyl,
($C_3$-$C_7$)-cycloalkoxy, where the cycloalkoxy radical is unsubstituted or substituted by one or more substituents selected from the group consisting of ($C_1$-$C_4$)-alkyl and ($C_1$-$C_4$)-alkoxy,
($C_1$-$C_6$)-alkylthio, where the alkylthio radical is branched or unbranched and is unsubstituted or substituted by one or more substituents selected from the group consisting of ($C_1$-$C_4$)-alkyl and ($C_1$-$C_4$)-alkoxy,
($C_3$-$C_7$)-cycloalkylthio, where the cycloalkylthio radical is unsubstituted or substituted by one or more substituents selected from the group consisting of ($C_1$-$C_4$)-alkyl and ($C_1$-$C_4$)-alkoxy,
the process more preferably being employable for preparation of compounds of the formula (II) in which the $R^{1a}$ radical is an unsubstituted ($C_1$-$C_4$)-alkoxy radical.

Particular preference is given to the employment of the process according to the invention for preparation of 4-[[(2-methoxybenzoyl)amino]sulphonyl]benzoyl chloride, i.e. particular preference is given to the inventive conversion of that compound of the formula (II) in which the $R^{1a}$ radical is methoxy (—O—$CH_3$) and, at the same time, $R^{1b}$ to $R^{1e}$ radicals are each all hydrogen (H).

In the above-defined group of aprotic and simultaneously polar solvents, particular aprotic polar solvents are preferred in the performance of the process according to the invention.

Preferred aprotic polar solvent classes are open-chain ketones, cyclic ketones, esters, amides, nitriles or ethers, each of which is unsubstituted or substituted, where the particular solvent molecules are unsubstituted or substituted by one or more substituents selected from the group consisting of
fluorine, chlorine, bromine, iodine, and
($C_1$-$C_4$)-alkyl.

Preference is given to converting the reactants of the formula (III) and of the formula (IV) in a mixture of aprotic polar solvents having a molecular weight of below 200 in each case, the mixture comprising at least two solvents from the group consisting of cyclohexanone, methyl isobutyl ketone, diisobutyl ketone, ethyl acetate, propyl acetate, butyl acetate, isopropyl acetate, isobutyl acetate, ethyl propionate, ethyl butyrate, propyl propionate, isopropyl propionate, dialkylacetamide, cycloalkylacetamide, acetonitrile, propionitrile, butyronitrile, valeronitrile, methyl tert-butyl ether, tetrahydrofuran and methyltetrahydrofuran.

More preferably, the reactants of the formula (III) and of the formula (IV) are converted exclusively in a specific solvent, the solvent being selected from the group consisting of cyclohexanone, methyl isobutyl ketone, diisobutyl ketone, ethyl acetate, propyl acetate, butyl acetate, isopropyl acetate, isobutyl acetate, ethyl propionate, ethyl butyrate, propyl propionate, isopropyl propionate, dialkylacetamide, cycloalkylacetamide, acetonitrile, propionitrile, butyronitrile, valeronitrile, methyl tert-butyl ether, tetrahydrofuran and methyltetrahydrofuran.

The most preferred solvents are the two solvents isopropyl acetate and isobutyl acetate.

However, it is also within the scope of the invention that the conversion of the reactants of the formula (III) and of the formula (IV) is effected not just in a specific aprotic polar solvent but in a mixture of different solvents. In this case, the solvent composition comprises at least two solvents selected from the group consisting of cyclohexanone, methyl isobutyl ketone, diisobutyl ketone, ethyl acetate, propyl acetate, butyl acetate, isopropyl acetate, isobutyl acetate, ethyl propionate, ethyl butyrate, propyl propionate, isopropyl propionate, dialkylacetamide, cycloalkylacetamide, acetonitrile, propionitrile, butyronitrile, valeronitrile, methyl tert-butyl ether, tetrahydrofuran and methyltetrahydrofuran.

Most preferably, the reactants of the formula (III) and of the formula (IV) are converted in a solvent selected from the group consisting of the group of the carboxylic esters, or in a solvent composition comprising at least two solvents selected from the group of the carboxylic esters.

Another significant advantage of the use of carboxylic esters as solvents is that the recovery thereof is less complex than the recovery of an aromatic solvent, for example the recovery of chlorobenzene or toluene. The improved solvent recovery distinctly reduces the amounts of waste overall, in the interests of sustainability.

However, the major advantage is that the formation of dimers in the case of performance of the reaction in a carboxylic ester or a carboxylic ester mixture as solvent is avoided.

Most preferred is the conversion of the reactants of the formula (III) and of the formula (IV) in a solvent selected from the group consisting of isopropyl acetate, isobutyl acetate and ethyl propionate or in a solvent composition comprising at least two solvents selected from the group consisting of isopropyl acetate, isobutyl acetate and ethyl propionate.

If the conversion is effected in just one solvent, isopropyl acetate is the solvent having the best suitability. In the case of use of isopropyl acetate as solvent, the compound of the formula (II) can be prepared by conversion of the reactants of the formula (III) and of the formula (IV) with particularly good yield and good quality.

A further advantage of isopropyl acetate was also found to be that, when isopropyl acetate is used as solvent, the recovery of the chlorinating agent used in excess in the reaction is particularly efficient.

Chlorinating agents usable in connection with the process according to the invention are all the chlorinating agents known by the person skilled in the art to be suitable, and it is also conceivable that a mixture consisting of a plurality of different chlorinating agents is used.

Preferred chlorinating agents are selected from the group of the sulphur- or phosphorus-based chlorinating agents. These include thionyl chloride, phosphorus oxychloride or phosphorus pentachloride, or carbon-based chlorinating agents such as oxalyl chloride or phosgene. The latter are usable for converting a carboxylic acid to a corresponding acid chloride.

Particularly preferred chlorinating agents are $Cl_2$, $SO_2Cl_2$, $SOCl_2$ (thionyl chloride), N-chlorosuccinimide, the most preferred chlorinating agent being thionyl chloride. It is also conceivable to use a mixture consisting of at least two of the aforementioned chlorinating agents.

Further usable chlorinating agents, in each case alternatively or in combination, are silicon tetrachloride, trichloromethylsilane, dichloromethylsilane, trichlorophenylsilane, aluminium trichloride, boron trichloride, titanium tetrachloride, tin tetrachloride, zinc dichloride or bismuth trichloride, or a mixture of these.

It is also possible to use mixtures of halosilanes and aluminium trichloride or zinc dichloride, for example mixtures of silicon tetrachloride and aluminium trichloride, where aluminium trichloride or zinc dichloride serve as catalyst and are used in amounts of 1% to 3% by weight, based on silicon tetrachloride.

When the process according to the invention is performed, for each equivalent of the formula (III or IV), between 2.5 and 3.0 equivalents of exchangeable chlorine atoms in a chlorinating agent or chlorinating agent mixture are used. Preference is given to using 2.5 eq. of thionyl chloride.

The compounds of the formulae (III) and (IV) are used in equimolar amounts.

The use of a catalyst is advantageously not required in the case of the inventive reaction.

The reaction temperatures in the performance of the process according to the invention may be varied within the ranges stipulated below. In general, temperatures employed are in the range from 20° C. to 90° C. Preference is given to temperatures in the range from 40° C. to 90° C. Particular preference is given to temperatures in the range from 80° C. to 90° C.

The process according to the invention is generally performed under standard pressure. However, it is also possible to work under elevated or reduced pressure. The preferred pressure range for performance of the inventive reaction is between 0.1 bar and 10 bar.

A further aspect of the invention relates to an improved process for preparing acylsulphamoylbenzamides of the formula (Ia), which is performable as a one-pot reaction. More particularly, the aforementioned aspect relates to a one-pot reaction for preparation of cyprosulfamide (N-[4-(cyclopropylcarbamoyl)phenylsulphonyl]-2-methoxybenzamide), proceeding from 4-[[(2-methoxybenzoyl)amino]sulphonyl]benzoyl chloride without prior isolation of the particular amide chloride precursor, which is in turn obtained by employing one of the aforementioned processes. Thus, this aspect of the invention relates to a one-pot reaction implementable on the industrial scale.

Accordingly, this further aspect of the invention relates to a process performable as a "one-pot reaction" on the industrial scale for preparation of compounds of the formula (Ia)

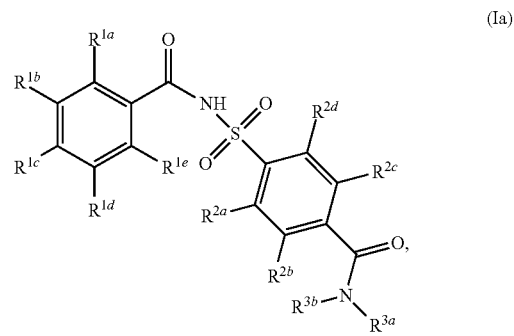

(Ia)

in which
$R^{1a}$ to $R^{1e}$ and $R^{2a}$ to $R^{2d}$ are each as defined above in connection with the elucidation of Claim 1,
$R^{3a}$ is selected from the group consisting of hydrogen and the following radicals: $(C_1-C_6)$-alkyl, $(C_1-C_6)$-haloalkyl, $(C_3-C_7)$-cycloalkyl, $(C_1-C_6)$-alkoxy, $(C_1-C_6)$-alkylthio, $(C_3-C_7)$-cycloalkylthio, $—(CH_2)p$-heterocyclyl, where each of these is unsubstituted or substituted by one or more substituents selected from the group consisting of halogen, $(C_1-C_6)$-alkyl, $(C_1-C_6)$-haloalkyl, $(C_1-C_6)$-alkoxy, cyano and nitro, and
$R^{3b}$ is selected from the group consisting of hydrogen and the following radicals: $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, $—(CH_2)$p-heterocyclyl, where each of these is unsubstituted or substituted by one or more substituents selected from the group consisting of halogen, $(C_1-C_4)$-alkoxy and $(C_1-C_4)$-alkylthio, or
$R^{3a}$ and $R^{3b}$ together with the connecting nitrogen atom form a 3- to 8-membered saturated or unsaturated ring,
by reacting a compound of the formula (II) in which $R^{1a}$ to $R^{1e}$ and $R^{2a}$ to $R^{2d}$ are each as defined above

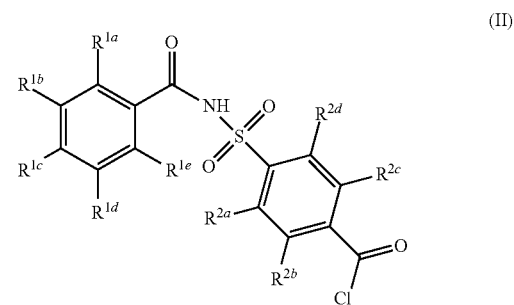

(II)

with an amine of the formula $R^{3a}R^{3b}NH$ in which the $R^{3a}$ and $R^{3b}$ radicals are each as defined above, characterized in that a compound of the formula (II) prepared by one of the processes described above in each case is initially charged
for reaction with the amine $R^{3a}R^{3b}NH$, without prior isolation,
in an aqueous NaOH solution.

In the preparation of cyprosulfamide, the amide chloride precursor, i.e. the compound of the formula (II) is obtained by the reaction of ortho-methoxybenzoic acid with 4-sulphamoylbenzoic acid.

The process according to the invention enables the preparation of cyprosulfamide proceeding from 4-[[(2-methoxybenzoyl)amino]sulphonyl]benzoyl chloride as reactant, wherein the reactant obtained from the conversion of ortho-methoxybenzoic acid and 4-sulphamoylbenzoic acid, prior to further reaction with an amine to give the cyprosulfamide target product, can be converted further directly without prior isolation.

Of course, prior isolation of said reactant is not ruled out, i.e. isolation is likewise possible.

In the recovery of the 4-[[(2-methoxybenzoyl)amino]sulphonyl]benzoyl chloride reactant required for preparation of cyprosulfamide, as explained above, it has been recognized that the choice of solvent is of unexpectedly great significance.

This finding relates to the fact that the problem of the above-elucidated dimer formation can be avoided, provided that the conversion is effected in a solvent selected from the group of the aprotic polar solvents, or in a solvent composition comprising at least one solvent selected from the group of the aprotic polar solvents.

It has also been recognized that the incomplete conversion of the abovementioned reactants used for synthesis of the 4-[[(2-methoxybenzoyl)amino]sulphonyl]benzoyl chloride precursor promotes the formation of unwanted by-products in the subsequent process step which serves for preparation of cyprosulfamide. One of the unwanted by-products probably forms through condensation of cyprosulfamide with 4-sulphamoyl-benzoic acid compounds of the formula (IV).

The conversion of the isolated (or alternatively unisolated) 4-[[(2-methoxybenzoyl) amino]sulphonyl]benzoyl chloride precursor to cyprosulfamide is preferably effected by the known chemical reaction method named after Schotten and Baumann (Schotten-Baumann method).

In general, the Schotten-Baumann method relates to the reaction of amines, alcohols or phenols with carbonyl chlorides in the presence of an aqueous alkali metal hydroxide solution as base. The base neutralizes the protons released in the reaction.

According to the teaching of this method, the base, in relation to the amide or ester is obtained, has to be used at least in a stoichiometric ratio because the reaction otherwise stops. Reactions by the Schotten-Baumann method are often performed in a biphasic system, with an aqueous phase and an organic phase. In this case, the protons released in the reaction are present in the aqueous phase, and are neutralized by the alkali metal hydroxide solution. The reactants and the reaction product, in contrast, are present in the organic phase.

In a known process performable on the industrial scale for preparing cyprosulfamide, acetonitrile is used as solvent, and an organic auxiliary base N,N-dimethylcyclohexylamine (HDA) is used. It is disadvantageous here that the required recovery of the costly auxiliary base from the product is inconvenient and difficult. Moreover, the use of the organic solvent acetonitrile, which is recovered for reasons of environmental protection and sustainability, constitutes additional complexity.

Earlier approaches to the efficient industrial scale preparation of cyprosulfamide using the Schotten-Baumann method with water as the sole solvent, i.e. dispensing with the addition of an additional organic solvent, have been found to be inefficient because of the hydrolysis sensitivity of the reactants and products.

Nevertheless, the improvement of a preparation process employed on the industrial scale for an active ingredient such as cyprosulfamide, for economic reasons and also because of environmental protection, remains a constant objective, and even a small improvement in the yield is of very great economic relevance because of the large molar amount.

The essential measure for achieving this improvement relates to the initial charging of the reactants in aqueous sodium hydroxide solution (NaOH) as the introductory process step. The special feature of this introductory process step in the preparation of cyprosulfamide is based on the noting of the fact that the chemical structure of the 4-[[(2-methoxybenzoyl)amino]sulphonyl]benzoyl chloride intermediate has one acidic proton, and the chemical structure of the cyprosulfamide end product actually has two acidic protons. For this reason, the hydrolysis sensitivity of the two compounds should be classified as high. However, the initial charging of the compounds in NaOH can attenuate the hydrolysis sensitivity thereof to an unexpected degree.

In the context of the development of the improved process for cyprosulfamide preparation, the reactants were at first initially charged in the sodium hydroxide solution with the sole objective of suppressing the formation of hydrochloric acid (HCl) in the reaction mixture from the start.

During the test phase of the improved process, however, it was recognized that, because of the initial presence of the sodium hydroxide solution, the reaction conditions cannot get into the acidic pH range and, as a result, the hydrolysis of the 4-[[(2-methoxybenzoyl)amino]sulphonyl]benzoyl chloride reactant can be suppressed to an unexpected degree.

The avoidance of the hydrolysis reaction is highly advantageous, because this suppresses the formation of an acid, namely 4-[[(2-methoxybenzoyl)amino]sulphonyl]-benzoic acid, and hence the achievement of higher cyprosulfamide yields is consequently possible.

The improvement of the process for preparing cyprosulfamide on the industrial scale by a "one-pot reaction" thus relates to several aspects:
  improvement of the yield compared to known processes, by avoidance of side reactions, and
  improvement of the overall efficiency of the process through avoidance of organic solvents and through avoidance of auxiliaries which subsequently have to be isolated from the end product, and
  workup of the solvent residues after conclusion of reaction through less complex working steps, for example precipitation and filtration.

Particular preference is given to the performance of the one-pot reaction with an amine of the formula $R^{3a}R^{3b}NH$ in which the $R^{3a}$ radical is cyclopropyl and the $R^{3b}$ radical is hydrogen, and a compound of the formula (II) in which $R^{1a}$ is methoxy, for preparation of the compound (Ib)

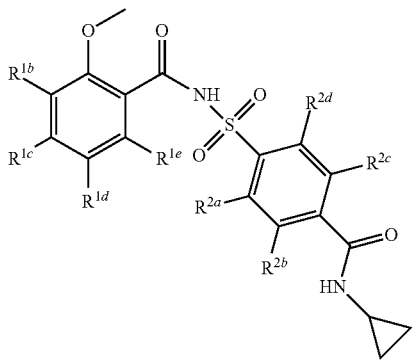

i.e. for preparation of cyprosulfamide.

A further aspect regarding to the improved process for cyprosulfamide preparation relates to a process in which a compound of formula (II) is isolated before it is initially charged in a sodium hydroxide solution with the sole objective of suppressing the formation of hydrochloric acid (HCl) in the reaction mixture from the start.

Preferably the isolated compound of formula (II) is initially charged in a sodium hydroxide solution in combination with the additional educt, e.g. the amine $R^{3a}R^{3b}NH$.

During the test phase of the alternative process, being characterized be the previous isolation of the 4-[[(2-methoxybenzoyl)amino]sulphonyl]benzoyl chloride reactant (amide chloride), it was again recognized that, because of the initial presence of the sodium hydroxide solution, the reaction conditions cannot get into the acidic pH range and, as a result, the hydrolysis of the 4-[[(2-methoxybenzoyl)amino]sulphonyl]benzoyl chloride reactant can be suppressed to an unexpected degree. As it has already been explained above in context with the "one-pot reaction" the avoidance of the hydrolysis reaction is highly advantageous, because this suppresses the formation of an acid, namely 4-[[(2-methoxybenzoyl)amino]sulphonyl]-benzoic acid, and hence the achievement of higher cyprosulfamide yields is consequently possible.

Furthermore, the presence of the base sodium hydroxide prevents protonation of the amine $R^{3a}R^{3b}NH$. Protonation of the amine is caused by the acid produced during the reaction. (Approximately 1 equivalent acid is produced by the reaction.) Prevention of protonation is especially relevant if the amine is added in a stoichiometric ratio. The use of the amine in a stoichiometric ratio, e.g. not the use of an excess of the amine, is desirable since the amine is a costly reactant.

EXAMPLES

Preparation of 4-[[(2-methoxybenzoyl)amino]sulphonyl]benzoyl chloride Into the initial charge of 1.02 eq. of ortho-methoxybenzoic acid compounds of the formula (III) (MBA) and 1 eq. of 4-sulphamoylbenzoic acid compounds of the formula (IV) (SBA) in isopropyl acetate are metered 2.5 eq. of thionyl chloride at 80-90° C. within 1-1.5 hours. After about 1-2 hours with stirring at 90° C., a clear solution is obtained. After a further hour of continued stirring time, no free acids are present any longer, but only the corresponding acid chlorides and the product. A clear solution is present at this time.

The excess thionyl chloride and a portion of the solvent (about 50%) are distilled off at about 800 mbar. The concentrated suspension is stirred at 90° C. for a further 3 hours. chlorides of the ortho-methoxybenzoic acid compounds of the formula (III) (MBCI) and of the chlorides of the 4-sulphamoylbenzoic acid compounds of the formula (IV) (SBCI) to the amide chloride (4-[[(2-methoxybenzoyl)amino]sulphonyl]benzoyl chloride). For the purpose of better stirrability and conversion, the thick suspension is diluted again The concentrating of the reaction mixture accelerates the conversion of the acid with isopropyl acetate.

This is followed by cooling to 0° C. and filtration. To displace the mother liquor, the filtercake is washed with isopropyl acetate (displacement wash) and dried at 60° C. under reduced pressure.

The isolated yield is 95-96% of theory at a purity of >98%.

TABLE 1

Tabular comparison of the yields based on HPLC analysis with use of various solvents for preparation of compounds of the formula (II), i.e. for preparation of 4-[[(benzoyl)-amino]sulphonyl]benzoyl chlorides.

| Exp. No. | Solvent | Chlorinating agent Thionyl chloride mol. eq. | Reaction time Reaction h | Reaction time Continued stirring h | Final weight g | HPLC % by wt. | Yield Isolated % of th. | Yield Waste-water % of th. | Dimeric species* Solids area % | Dimeric species* Solids % of th. |
|---|---|---|---|---|---|---|---|---|---|---|
| A1 | isopropyl acetate | 2.5 | 3.5 (80-90° C.) | 60 (90° C.) | 180.2 | 99.5 | 91.4 | 2.9 | 0.08 | 0.14 |
| A2 | isopropyl acetate | 2.5 | 7 (80-90° C.) | 0 | 190.4 | 98.4 | 95.0 | 1.0 | 0.10 | 0.18 |
| A3 | isopropyl acetate | 2.5 | 7 (80-90° C.) | 0 | 192.3 | 96.5 | 95.7 | 1.5 | 0.10 | 0.19 |
| A4 | isopropyl acetate | 2.5 | 7 (80-90° C.) | 0 | 192.7 | 99.1 | 98.4 | 1.3 | 0.35 | 0.67 |
| B1 | toluene | 2.5 | 5 (85° C.) | 1 (85° C.) | 162.5 | 96.4 | 88.6 | 3.1 | 1.05 | 1.85 |
| B2 | toluene | 2.5 | 7 (85° C.) | 1 (85° C.) | 155.8 | 95.3 | 83.9 | 3.1 | 1.64 | 2.77 |
| B3 | toluene | 3 | 4 (110° C.) | 0 | 161.9 | 95.9 | 88.7 | 3.9 | 1.09 | 1.93 |
| C1 | chloro-benzene | 3 | 4 (85-90° C.) | 12 (85-90° C.) | 150.2 | 88.2 | 75.6 | 8.3 | 5.87 | 9.65 |

TABLE 1-continued

Tabular comparison of the yields based on HPLC analysis with use of various solvents for preparation of compounds of the formula (II), i.e. for preparation of 4-[[(benzoyl)-amino]sulphonyl]benzoyl chlorides.

| Exp. No. | Solvent | Chlorinating agent Thionyl chloride mol. eq. | Reaction time Reaction h | Continued stirring h | Final weight g | HPLC % by wt. | Yield Isolated % of th. | Waste-water % of th. | Dimeric species* Solids area % | % of th. |
|---|---|---|---|---|---|---|---|---|---|---|
| C2 | chlorobenzene | 3 | 4 (85-90° C.) | 12 (85-90° C.) | 143.9 | 89.9 | 73.9 | 10.0 | 5.68 | 8.94 |
| C3 | chlorobenzene | 3 | 4 (85-90° C.) | 0 | 153.6 | 96.7 | 84.8 | 8.1 | 1.57 | 2.64 |

*Factor of 1.5

The above table compares the isopropyl acetate solvent used in accordance with the invention with the toluene and chlorobenzene solvents, with use of thionyl chloride as chlorinating agent throughout, and with a reaction time of several hours in each case and with reaction temperatures within a narrow range.

Comparison of the Yields

The tabular comparison demonstrates, through experiments A2, A3, A4 and B3 and experiment C3, first of all that the yields of the reaction are higher in all solvents, and so no continued stirring of the reaction solution takes place. In industrial preparation, however, continued stirring of the reaction solution is frequently unavoidable for technical reasons.

Thus, the table demonstrates, through experiments A1 and B2 and C1 and C2 that continuing to stir the reaction solution for one hour after a reaction time of several hours (i.e. after a reaction time of 3.5 to 7 hours) distinctly worsens the yield of the reaction. Only experiment B1 is an exception, and does not confirm that a reduction in the yield has to be expected even when continuing to stir for only one hour.

Moreover, it is noticeable on comparison of the various solvents that the deterioration in the yield is comparatively small in spite of an extremely long continued stirring time of 60 hours (Experiment A1) when isopropyl acetate is used as solvent, and the yield is nevertheless above 90%, namely 91.4%. In comparison, the yield in the case of use of the toluene and chlorobenzene solvents is below 90% in both cases, namely 88.7% (Experiment B3) and 84.8% (Experiment C3), with no continued stirring in either of the two latter experiments. If, however, stirring is continued in the case of use of the toluene and chlorobenzene solvents, the yield is even worse, namely, for example, 83.9% (Experiment B2) and 73.9% (Experiment C2).

Comparison of Dimer Formation

A particular advantage of the process according to the invention is found to be the low dimer formation when isopropyl acetate is used as solvent.

Experiments A2 and A3 demonstrate, in comparison to experiment A1, that even an extremely long continued stirring time of 60 hours (Experiment A1) when isopropyl acetate is used as solvent does not have any significant influence on unwanted dimer formation An exception is experiment A4 with a value of 0.67. However, the value of 0.67 is still much lower than the corresponding values when toluene and chlorobenzene are used as solvents. The corresponding values when toluene and chlorobenzene are used is in the range of 1.85 to 9.65.

Dimer formation is noticeably high when chlorobenzene is used as solvent in the case of continued stirring for several hours (cf. Experiments C1 and C2).

In summary, it can be stated in relation to Table 1 that, in the case of comparative use of one of the inventive solvents, namely in the case of use of isopropyl acetate as compared with toluene and chlorobenzene, the improvement in the yield is unexpectedly high and, at the same time, unwanted dimer formation is surprisingly low.

Thus, the use of isopropyl acetate is advantageous in two ways and enables a robust process which is particularly suitable and advantageous for industrial use for economic reasons as well, because of the potential for savings in various resources.

The usability of the 4-[[(2-methoxybenzoyl)amino]sulphonyl]benzoyl chloride prepared in accordance with the invention for preparation of cyprosulfamide is demonstrated by a preparation example.

Synthesis Example

Preparation of Cyprosulfamide Proceeding from 4-[[(2-methoxybenzoyl)amino]-sulphonyl]benzoyl chloride A concentrated suspension of the 4-[[(2-methoxybenzoyl)amino]sulphonyl]benzoyl chloride (amide chloride) prepared in the above-described synthesis is diluted with toluene. The rest of isopropyl acetate originating from the preceding synthesis is distilled off together with a portion of the toluene. This is followed by cooling to 20° C. Into an initial charge composed of water, triethylamine 0.5 eq., cyclopropylamine (CPA) 1.1 eq., sodium hydroxide solution 1.2 eq. and toluene is metered the amide chloride suspension in toluene at 10-30° C. within about 1 hour. In the course of this, the pH is kept at 8.5-9.0 by means of 32% sodium hydroxide solution. After the addition has ended, the mixture is heated to 80° C. In the course of this, the pH is allowed to drop to about 8.0. At 80° C., the pH is adjusted to 10, in order to force the triethylamine completely into the organic phase. In order to prevent unwanted side reactions, for example the hydrolysis of the remaining isopropyl acetate, the phase separation should be effected immediately.

The aqueous phase is subjected to brief incipient distillation at 80° C. and about 800 mbar. Subsequently, at 80° C., 37% hydrochloric acid is used to lower the pH from 10 to pH about 8.5, with partial precipitation of the N-[4-(cyclopropylcarbamoyl)phenyl-sulphonyl]-2-methoxybenzamide (cyprosulfamide) product. The pH change is required to assure the stability of isopropyl acetate which is added again at this point.

In the course of addition of isopropyl acetate, the temperature is allowed to drop to 70° C. At 70° C., the active ingredient is precipitated quantitatively by means of HCl (37%) at pH 5.3-5.7. The active ingredient suspension is cooled to 50° C. and filtered. Since the product floats completely in the upper organic phase when the stirrer is switched off, the lower aqueous phase can first of all be discharged via the suction filter. The filtercake is washed first with isopropyl acetate as displacement wash and then with water as reslurry wash. The drying is effected at 60° C. under reduced pressure.

Preparation of Cyprosulfamide Charging the Isolated Solid Form of Amide Chloride in Aqueous Sodium Hydroxide Into an initial charge composed of water, sodium hydroxide solution (1.2 eq., 32%) and cyclopropylamine 1.1 eq. is introduced 4-[[(2-methoxybenzoyl)amino]sulphonyl]-benzoyl chloride (amide chloride) in solid form at 20-30° C. within about 30 min. During the addition (after about half of the amide chloride has been metered in), the pH is kept at 8-9 in parallel with 32% sodium hydroxide solution.

The mixture is stirred at 30° C. for a further 30 min and then heated to 80° C. During the heating phase, the pH is regulated further with 32% sodium hydroxide solution and kept at 8-9. Under these reaction conditions, the active ingredient at first goes completely into the solution as the sodium salt. At 80° C., the excess of CPA is subjected to brief incipient distillation. Foam formation can be prevented by the addition of a little toluene.

The active ingredient is then precipitated out of this solution by means of 10% hydrochloric acid at pH 5.8-6.2. The solids are filtered off at 80° C. and then washed twice with water. First a displacement wash at 80° C. and then a reslurry wash at 80° C. are conducted. The wash filtrate of the reslurry wash is reusable. The active ingredient is dried at 60° C.

The isolated yield is 98-99% of theory.

The invention claimed is:

1. A process for preparing a compound of formula (Ia)

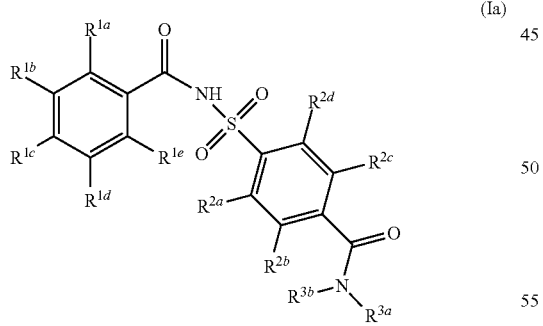

in which $R^{1a}$ to $R^{1e}$ and $R^{2a}$ to $R^{2d}$ are each independently selected from the group consisting of hydrogen, halogen, $(C_1-C_6)$-alkyl, $(C_1-C_6)$-haloalkyl, $(C_1-C_6)$-alkoxy, $(C_3-C_7)$-cycloalkyl, $(C_3-C_7)$-cycloalkoxy, $(C_1-C_6)$-alkylthio, $(C_3-C_7)$-cycloalkylthio, $S(O)q$-$(C_1-C_6)$-alkyl with q=0, 1 or 2, $(C_1-C_6)$-alkylcarbonyl, —CO-aryl, cyano and nitro, or in which any two adjacent $R^{1a}$ to $R^{1e}$ radicals form a —O—CH$_2$CH$_2$— radical, and $R^{3a}$ is selected from the group consisting of hydrogen, $(C_1-C_6)$-alkyl, $(C_1-C_6)$-haloalkyl, $(C_3-C_7)$-cycloalkyl, $(C_1-C_6)$-alkoxy, $(C_1-C_6)$-alkylthio, $(C_3-C_7)$-cycloalkylthio, and —(CH$_2$)-heterocyclyl, wherein each of these is unsubstituted or substituted by one or more substituents selected from the group consisting of halogen, $(C_1-C_6)$-alkyl, $(C_1-C_6)$-haloalkyl, $(C_1-C_6)$-alkoxy, cyano and nitro, and $R^{3b}$ is selected from the group consisting of hydrogen, $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, and —(CH$_2$)-heterocyclyl, wherein each of these is unsubstituted or substituted by one or more substituents selected from the group consisting of halogen, $(C_1-C_4)$-alkoxy and $(C_1-C_4)$-alkylthio, or $R^{3a}$ and $R^{3b}$ together with the connecting nitrogen atom form a 3- to 8-membered saturated or unsaturated ring, the process comprising reacting an isolated compound of formula (II)

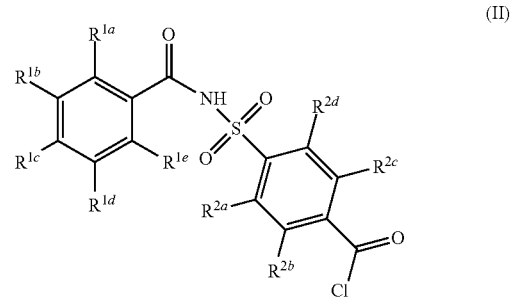

in which the $R^{1a}$ to $R^{1e}$ and $R^{2a}$ to $R^{2d}$ radicals are each as defined above, with an amine of the formula $R^{3a}R^{3b}NH$ in which the $R^{3a}$ and $R^{3b}$ radicals are each as defined above, wherein a compound of formula (II) is initially charged for reaction with the amine $R^{3a}R^{3b}NH$, in an aqueous NaOH solution, and further comprising preparing the compound of formula (II) by reacting a compound of formula (III)

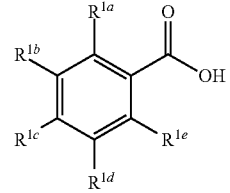

in which $R^{1a}$ to $R^{1e}$ are each as defined above, with a compound of formula (IV)

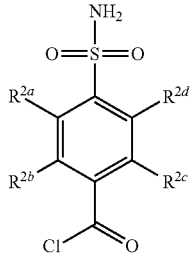

in which

R$^{2a}$ to R$^{2d}$ are each as defined above, in one or more solvents selected from the group consisting of esters of propionic acid and esters of acetic acid.

2. The process according to claim 1, wherein R$^{1a}$ in the reactant of the formula (II) is methoxy (—O—CH$_3$) and the R$^{3a}$ radical in the amine of the formula R$^{3a}$R$^{3b}$NH is cyclopropyl, and R$^{3b}$ is hydrogen.

3. The process according to claim 1, wherein the amine itself is charged in the aqueous NaOH solution.

4. The process according to claim 1, wherein

R$^{1a}$ to R$^{1e}$ and R$^{2a}$ to R$^{2d}$ are each independently selected from the group consisting of hydrogen, fluorine, chlorine, bromine, (C$_1$-C$_6$)-alkyl, wherein the alkyl radical is branched or unbranched and is unsubstituted or substituted by one or more substituents selected from the group consisting of (C$_1$-C$_4$)-alkoxy and (C$_3$-C$_7$)-cycloalkyl, (C$_1$-C$_6$)-haloalkyl, wherein the one or more halogen substituents are selected from the group consisting of fluorine, chlorine, bromine and iodine, (C$_3$-C$_7$)-cycloalkyl, wherein the cycloalkyl radical is unsubstituted or substituted by one or more substituents selected from the group consisting of (C$_1$-C$_4$)-alkyl, (C$_3$-C$_7$)-cycloalkyl, and (C$_1$-C$_4$)-alkoxy, (C$_1$-C$_6$)-alkoxy, wherein the alkoxy radical is branched or unbranched and is unsubstituted or substituted by one or more substituents selected from the group consisting of (C$_1$-C$_4$)-alkoxy and (C$_3$-C$_7$)-cycloalkyl, (C$_3$-C$_7$)-cycloalkoxy, wherein the cycloalkoxy radical is unsubstituted or substituted by one or more substituents selected from the group consisting of (C$_1$-C$_4$)-alkyl and (C$_1$-C$_4$)-alkoxy, (C$_1$-C$_6$)-alkylthio, wherein the alkylthio radical is branched or unbranched and is unsubstituted or substituted by one or more substituents selected from the group consisting of (C$_1$-C$_4$)-alkyl and (C$_1$-C$_4$)-alkoxy, and (C$_3$-C$_7$)-cycloalkylthio, wherein the cycloalkylthio radical is unsubstituted or substituted by one or more substituents selected from the group consisting of (C$_1$-C$_4$)-alkyl and (C$_1$-C$_4$)-alkoxy.

5. The process according to claim 1, wherein R$^{1a}$ is an unsubstituted (C$_1$-C$_4$)-alkoxy radical, and R$^{1b}$ to R$^{1e}$ and R$^{2a}$ to R$^{2d}$ are each hydrogen.

6. The process according to claim 1, wherein R$^{1a}$ is methoxy (—O—CH$_3$), and R$^{1b}$ to R$^{1e}$ and R$^{2a}$ to R$^{2d}$ are each hydrogen.

7. The process according to claim 1, wherein the solvent has a molecular weight of less than 200.

8. The process according to claim 1, wherein the solvent is one or more selected from the group consisting of ethyl acetate, propyl acetate, butyl acetate, isopropyl acetate, isobutyl acetate, ethyl propionate, propyl propionate, and isopropyl propionate.

9. The process according to claim 1, wherein the solvent is isopropyl acetate.

10. The process according to claim 1, wherein the solvent is one or more selected from the group consisting of isopropyl acetate, isobutyl acetate and ethyl propionate.

11. The process according to claim 1, wherein the solvent is a solvent composition comprising at least two solvents selected from the group consisting of isopropyl acetate, isobutyl acetate and ethyl propionate.

12. The process according to claim 1, wherein a chlorinating agent is used in the process to prepare the compound of formula (II) and the chlorinating agent is thionyl chloride.

13. The process according to claim 1, wherein the reaction of reactants III and IV is effected
within a temperature range from 20° C. to 90° C. and
within a pressure range from 0.1 to 10 bar.

14. The process according to claim 1, wherein the reaction to prepare the compound of formula (Ia) is effected in the presence of toluene.

\* \* \* \* \*